United States Patent
Nevyas-Wallace

(10) Patent No.: US 10,143,589 B2
(45) Date of Patent: Dec. 4, 2018

(54) METHOD AND APPARATUS FOR MAKING IMPROVED SURGICAL INCISIONS IN CORRECTIVE EYE SURGERY

(76) Inventor: Anita Nevyas-Wallace, Narberth, PA (US)

( * ) Notice: Subject to any disclaimer, the term of this patent is extended or adjusted under 35 U.S.C. 154(b) by 737 days.

(21) Appl. No.: 13/402,389

(22) Filed: Feb. 22, 2012

(65) Prior Publication Data

US 2013/0150835 A1    Jun. 13, 2013

Related U.S. Application Data

(60) Provisional application No. 61/445,450, filed on Feb. 22, 2011.

(51) Int. Cl.
    *A61B 18/20*    (2006.01)
    *A61F 9/008*    (2006.01)
    *A61B 34/00*    (2016.01)

(52) U.S. Cl.
    CPC ............. *A61F 9/008* (2013.01); *A61B 18/20* (2013.01); *A61B 34/25* (2016.02); *A61F 9/00802* (2013.01); *A61F 2009/00872* (2013.01); *A61F 2009/00882* (2013.01)

(58) Field of Classification Search
    CPC ............ A61F 9/008; A61F 2009/00872; A61F 2009/00897; A61F 9/00802; A61F 2009/00882; A61B 19/50; A61B 9/008; A61B 34/25; A61B 18/20
    See application file for complete search history.

(56) References Cited

U.S. PATENT DOCUMENTS

| | | | |
|---|---|---|---|
| 5,222,967 A | | 6/1993 | Casebeer |
| 5,423,840 A | | 6/1995 | Casebeer |
| 5,549,632 A | * | 8/1996 | Lai ................................... 606/5 |
| 6,210,401 B1 | * | 4/2001 | Lai .................................. 606/12 |
| 7,135,016 B1 | | 11/2006 | Asia et al. |
| 7,655,002 B2 | | 2/2010 | Myers |
| 2001/0010003 A1 | * | 7/2001 | Lai ................................ 606/107 |
| 2004/0059321 A1 | | 3/2004 | Knopp et al. |
| 2004/0199150 A1 | * | 10/2004 | Lai .................................... 606/5 |
| 2007/0027439 A1 | | 2/2007 | Durrie et al. |
| 2008/0033408 A1 | * | 2/2008 | Bueler et al. ..................... 606/5 |

(Continued)

OTHER PUBLICATIONS

Summary of Past Activities of Inventor Dr. Anita Nevyas-Wallace.

*Primary Examiner* — Scott T Luan
(74) *Attorney, Agent, or Firm* — FisherBroyles LLP

(57) ABSTRACT

A method and apparatus for making improved surgical incisions in corrective eye surgery are provided. It was observed that a uniform elongated AK (or LRI) incision provides a non-uniform corrective effect due to non-uniform post-surgical relaxation of ophthalmic tissue. The method and apparatus leverage this observation to provide for creation of a surgical incision that is structured to be non-uniform along its length in such a manner as to at least partially counteract an expected variation in ophthalmic tissue relaxation to provide overall increased uniformity of corrective effect. An automated laser surgery system includes a laser control system configured to control laser delivery to cause selective ablation of ophthalmic tissue to provide an elongated structured incision that varies along its length in at least one of a depth, a profile, a width, and an angle of attack relative to a surface of the ophthalmic tissue.

14 Claims, 7 Drawing Sheets

(56) References Cited

U.S. PATENT DOCUMENTS

| | | |
|---|---|---|
| 2008/0281303 A1 | 11/2008 | Culbertson et al. |
| 2008/0312675 A1 | 12/2008 | Newcott et al. |
| 2009/0275929 A1 | 11/2009 | Zickler |
| 2009/0287232 A1 | 11/2009 | Davis |
| 2012/0296394 A1* | 11/2012 | Culbertson et al. ............ 607/53 |
| 2013/0274723 A1* | 10/2013 | Donitzky et al. ................ 606/5 |

* cited by examiner

METHOD AND APPARATUS FOR MAKING IMPROVED SURGICAL INCISIONS IN CORRECTIVE EYE SURGERY

CROSS-REFERENCE TO RELATED APPLICATION

This application claims the benefit of priority under 35 U.S.C. 119(e) of U.S. Provisional patent Application No. 61/445,450, filed Feb. 22, 2011, the entire disclosure of which is hereby incorporated herein by reference.

FIELD OF THE INVENTION

The present invention relates generally to ophthalmic surgical procedures, and more particularly to a system and method for making improved incisions having novel corrective incision geometries.

DISCUSSION OF RELATED ART

Limbal relaxing incisions (LRI's) commonly are used to correct small to moderate amounts of astigmatism, particularly in conjunction with cataract surgery. Astigmatic keratotomy (AK) incisions at smaller optical zones have been used for moderate and higher amounts of astigmatism. In either case, an arcuate incision made at the steep meridian of the cornea allows the area of the cornea central to it to flatten and also to elevate, changing both the shape and the curvature of the cornea as the ocular tissue relaxes around the incision site. The coupling effect causes the flat meridian of the cornea to be steepened nearly as much as the steep meridian is flattened. By properly placing such AK (including LRI) relaxing incisions, such steepening and flattening can be used for corrective purposes.

FIG. 1 shows the anatomy of a human eye generally designated by reference numeral 10. The outer surface of the eye 10 is formed by a cornea 12 which terminates at the corneal margin or limbus 14 in the vicinity of an anatomical protuberance on the inner surface of the cornea known as the scleral spur. The ciliary muscle joins the iris. The ciliary muscle is connected by the zonular fibers to the capsule of the crystalline lens. Contraction of the ciliary muscle changes the shape and position of the lens, which results in focusing of the vision of the subject. The iris surrounds the pupil, where light passes through the lens onto the retina (not shown) for transmission of an image to the optic nerve and the brain.

AK incisions (including LRI's) require precise formation and placement of arcuate incisions, often spanning approximately 30 degrees to 75 degrees of arc, and 3 mm to 6 mm in length. Exemplary AK and LRI incisions are designated by reference numeral 30 in FIG. 1.

A prevalent method of making such arcuate incisions involves the surgeon's manual use of a surgical knife having a diamond blade fixed to protrude between an associated footplate for a predetermined depth of cut. Such incisions are made (or at least are intended to be made) by sweeping the blade in a constant-radius arc while holding the knife/blade at a consistent angular orientation relative to the eye (i.e. using a consistent "angle of attack"). Because such blades have a fixed thickness, resulting incisions have a uniform cross-sectional profile, or width of cut. Many such incisions made with this manual approach are shallower at their ends than at their center, for several reasons. First, the intended depth (D) typically is reached only after the diamond blade 20 is advancing through tissue, rather than on its initial insertion, as best shown in FIG. 2. Furthermore, if the diamond knife has an angled end face (as is typical), the ends (E) of the incision are necessarily shallower where the blade end itself is angled, even if the blade tip has penetrated to full depth, as best shown in FIG. 3. Accordingly, in using such a knife, the incision typically has a geometry in which the depth is substantially uniform, but is greatest toward a central portion along the length of the incision, and lesser towards the leading and trailing ends of the incision, as best shown in FIGS. 2 and 3.

Various diamond-bladed (and other) knives are known in the art for use in incisional keratotomy. An improvement to the common knife includes a specially-configured blade having an enhancement portion. The enhancement portion includes a rearward blade edge that is sharpened only distally (for the distal 250 microns) to provide an enhancement cutting edge, so that an unsharpened portion of the rearward blade edge can guide the blade through the incision as the enhancement portion finishes the cut by bringing it to full cut depth. An exemplary knife having such an enhancement portion is commercially-available as a Genesis™ knife, manufactured and/or sold by Accutome, Inc. of Malvern, Pa., or the virtually-identical DuoTrak™ knife described in U.S. Pat. Nos. 5,222,967 and 5,423,840, the entire disclosures of both of which are hereby incorporated herein by reference.

The angled edge of such a knife is sharp along its entire length, and is used to make the initial incision. The vertical (opposite) edge of the knife is then used to retrace the incision back to its origin, so that the dull part of the vertical edge guides the knife and avoids cutting a new incision, while the vertical "enhancement" edge (the sharp distal 250 microns) cuts to bring the incision to full depth. Accordingly, in using such a knife, the incision typically has a constant (uniform) depth (D) along the entire length of the incision, as best shown in FIG. 4.

It has been observed that both of the above-described incision geometries (shallow-deep-shallow, and constant depth) create an unevenness of corrective effect along an astigmatic keratotomy incision. This effect was discussed in a 1996 publication by Canrobert Oliveira, who described resulting induced astigmatism at new axes. *Radial keratotomy: the combined technique.* Assil K K. Int Ophthalmol Clin. 1994 Fall; 34(4):55-77.

In response to the observed unevenness of effect, Oliveira devised the "Canrobert 'C' procedure", in which shorter arcuate incisions are added adjacent to each end of an astigmatic keratotomy incision, peripheral to the main incision. A modification of this was proposed by Freitas and Carvalho in 2008, in which a shorter arcuate incision is added adjacent to each end of an LRI, just central to it. Freitas G D: *Limbal Relaxing Incision with Inverse C Procedure.* Film, ASCRS 2008. The Canrobert "C" procedure has enjoyed some popularity, and markers with templates for the Canrobert "C" incisions are commercially available.

However, there are certain difficulties/inadequacies with such procedures, including the need for additional corrective incisions to counteract the unevenness of corrective effect of the initial AK/LRI incision. Such additional incisions create additional opportunities for errors and causes increased trauma to the eye, and associated increased risks associated with infection and healing.

SUMMARY

The present invention provides a system and method providing an alternative to the "C" procedures, which generally involve making incisions with a uniform cut width, a substantially uniform depth, and substantially uniform angle of attack. Generally, I have observed that a uniform AK (including LRI) incision results in a non-uniform corrective effect. In accordance with the present invention, I leverage this observed relationship to provide a system and method for making a structured AK (including LRI) incision for the purpose of providing a uniform (or at least more consistent) corrective effect. As used herein, "structured" is used to denote a deliberately-made lack of uniformity in at least one of incision profile/width, incision depth, or angle of attack for the purpose of providing a more consistent corrective effect due to a more consistent relaxing of ocular tissue as a result of the configuration of the incision.

Systems and methods for making structured incisions are provided. An exemplary method for performing ophthalmic laser surgery using an automated laser delivery system comprises providing an automated laser surgery system comprises: a laser delivery system operable to deliver a laser beam for ablating ophthalmic tissue; a user interface configured to receive user input; and a laser control system configured to control delivery of the laser beam in accordance with input received via the user interface. The method further comprises operating the automated laser surgery system to selectively ablate ophthalmic tissue to provide an elongated structured incision, the structured incision being non-uniform in cross-section along its length in at least one of a depth, a profile, a width, and an angle of attack relative to a surface of the ophthalmic tissue.

Another exemplary method for performing ophthalmic laser surgery comprises: generating a pulsed laser beam, wherein the duration of each pulse in the beam is less than approximately one picosecond in duration; and directing and focusing the beam onto a plurality of focal spots to ablate ophthalmic tissue, the plurality of focal spots being selected to collectively provide an elongated structured incision in the ophthalmic tissue, the structured incision being non-uniform along its length in at least one of a depth, a profile, a width, and an angle of attack relative to a surface of the ophthalmic tissue.

An exemplary automated laser surgery system comprises a laser delivery system operable to deliver a laser beam for ablating ophthalmic tissue; a user interface configured to receive user input; and a laser control system operably connected to said laser delivery system and said user interface, said laser control system being configured to control delivery of the laser beam in accordance with input received via said user interface, said laser control system being configured to control said laser delivery system to cause the laser beam to selectively ablate ophthalmic tissue to provide an elongated structured incision that varies along its length in at least one of a depth, a profile, a width, and an angle of attack relative to a surface of the ophthalmic tissue. The laser control system may be further configured to control the laser beam to provide variation in the elongated structured incision that at least partially counteracts an expected variation in relaxation of ophthalmic tissue along an incision site to provide increased uniformity of corrective effect to the ophthalmic tissue.

BRIEF DESCRIPTION OF THE FIGURES

An understanding of the following description will be facilitated by reference to the attached drawings, in which.

DETAILED DESCRIPTION

The present invention relates to a system and method that provide novel incision geometries useful in procedures involving astigmatic keratotomy (AK) incisions or limbal relaxation incisions (LRI).

Figure 1:
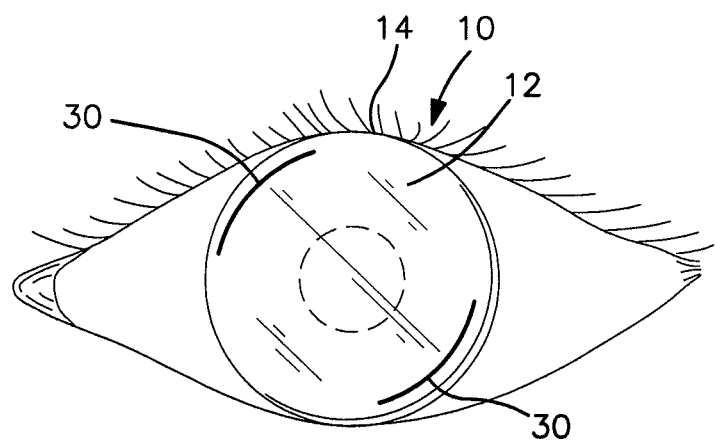
FIG. 1 is a diagrammatic view of a human eye showing exemplary incisions made in typical incisional keratotomy procedures.
Figure 2:
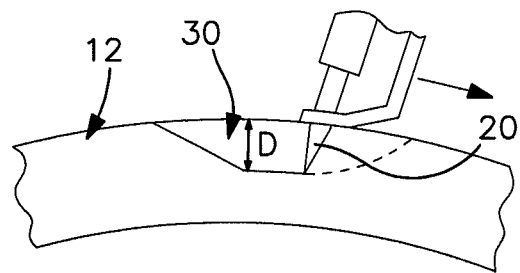
FIG. 2 is a partial cross-sectional view of the eye of FIG. 1, showing a conventional incision having shallower end portions and a deeper central portion due to gradual insertion of the surgical knife.
Figure 3:
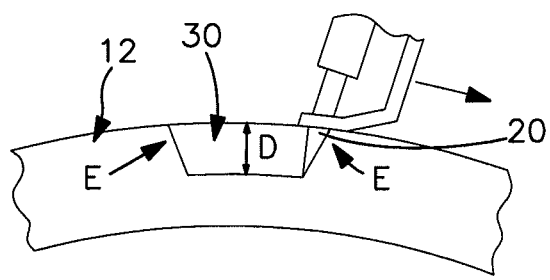
FIG. 3 is a partial cross-sectional view of the eye of FIG. 1, showing a conventional incision having shallower end portions and a deeper central portion due to angled edges of the surgical knife.
Figure 4:
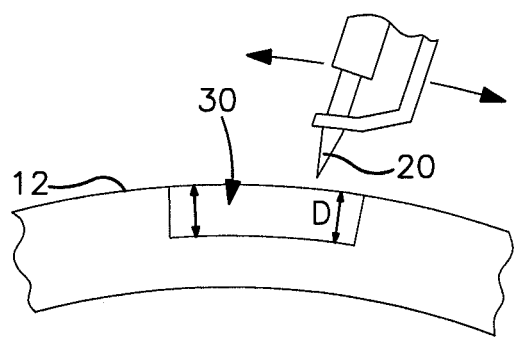
FIG. 4 is a partial cross-sectional view of the eye of FIG. 1, showing a conventional incision having a constant depth.
Figure 5:
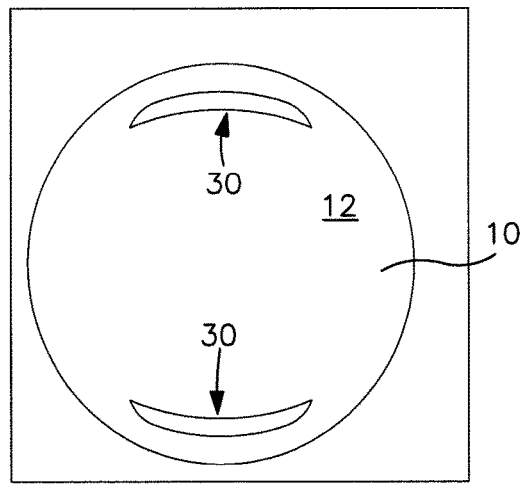
FIG. 5 is a diagrammatic view of the human eye of FIG. 1, showing varied degrees of gaping along the length of the incision.

I have observed that in astigmatic keratotomy (including AK incisions and LRI incisions—collectively here "AK incision") at any optical zone, the portion of the AK incision that exerts the most relaxing (and thus corrective) effect is the central portion. When an AK incision gapes, the gaping is more prominent at a central portion than at the end portions of the incision, as best shown in FIG. 5. Not uncommonly, elevation corneal topography following AKs shows greater elevation and more astigmatic effect toward the central portion of the incision than at the incision's end portions.

In accordance with the present invention, I have developed a surgical approach that exploits this observation to compensate for and correct the unevenness of effect along an AK incision previously observed by Canrobert Oliveira and others. Accordingly, the present approach is an alternative to the "C" procedures.

Generally, I have observed that a uniform AK incision results in a non-uniform corrective effect. In accordance with the present invention, I leverage this observed relationship to provide a system and method for making a structured AK (including LRI) incision for the purpose of providing a uniform (or at least more consistent) corrective effect. As used herein, "structured" is used to denote a deliberately-made lack of uniformity in at least one of incision profile/width, incision depth, or angle of attack for the purpose of providing a more consistent corrective effect due to a more consistent relaxing of ocular tissue as a result of the configuration of the incision. Accordingly, a "structured" incision includes more than mere incidental or unintended variation from uniformity.

More specifically, the approach of the present invention involves making a structured incision that is designed to cause a greater relaxing effect (due to the configuration of the incision) towards the incision's end portions than at it's central portion. This non-uniformity of relaxing effect resulting from the configuration of the incision is created to counteract the natural tendency of such an incision to have a greater relaxing effect toward the central portion of the incision than at its end portion (believed to be due, at least in part, to the shape of the eye/surgical site, and the material properties of ocular tissue). By inducing a greater relaxing effect toward the end portions that complements or counteracts the naturally-occurring greater relaxing effect toward the central portion, a more consistent relaxing effect along the entire length of the incision, and thus a reduction in higher order aberration, is obtained. Thus, the need for supplemental corrective incisions, as taught by Canrobert Oliveira and others, is reduced or eliminated.

Systems and methods for making various structured incisions are provided in accordance with the present invention. In one embodiment, the structured incision is configured to have a shallower central portion and deeper end portions that collectively tend to induce a greater relaxing effect toward the end portions of the incision. In another embodiment, the structured incision is configured to have a varying angle of attack that tends to induce a greater relaxing effect toward the end portions of the incision. In yet another embodiment, the structured incision is configured to have a varying cross-sectional profile area (e.g., width or shape) that tends to induce a greater relaxing effect toward the end portions of the incision. In still other embodiments of the invention, the structured incision includes any combination of more than one of a varying depth, a varying angle of attack and a varying cross-sectional profile along its length to induce a relatively greater relaxing effect toward the end portions of the incision.

The novel structured incision geometries described herein may be created using both traditional manual surgical techniques and automated surgical techniques. For illustrative purposes, an exemplary manual surgical method is discussed below with reference to FIGS. 6 and 7A-7F, followed by a discussion of an automated surgical system-based method with reference to FIGS. 8 and 9A-10.

Figure 6:
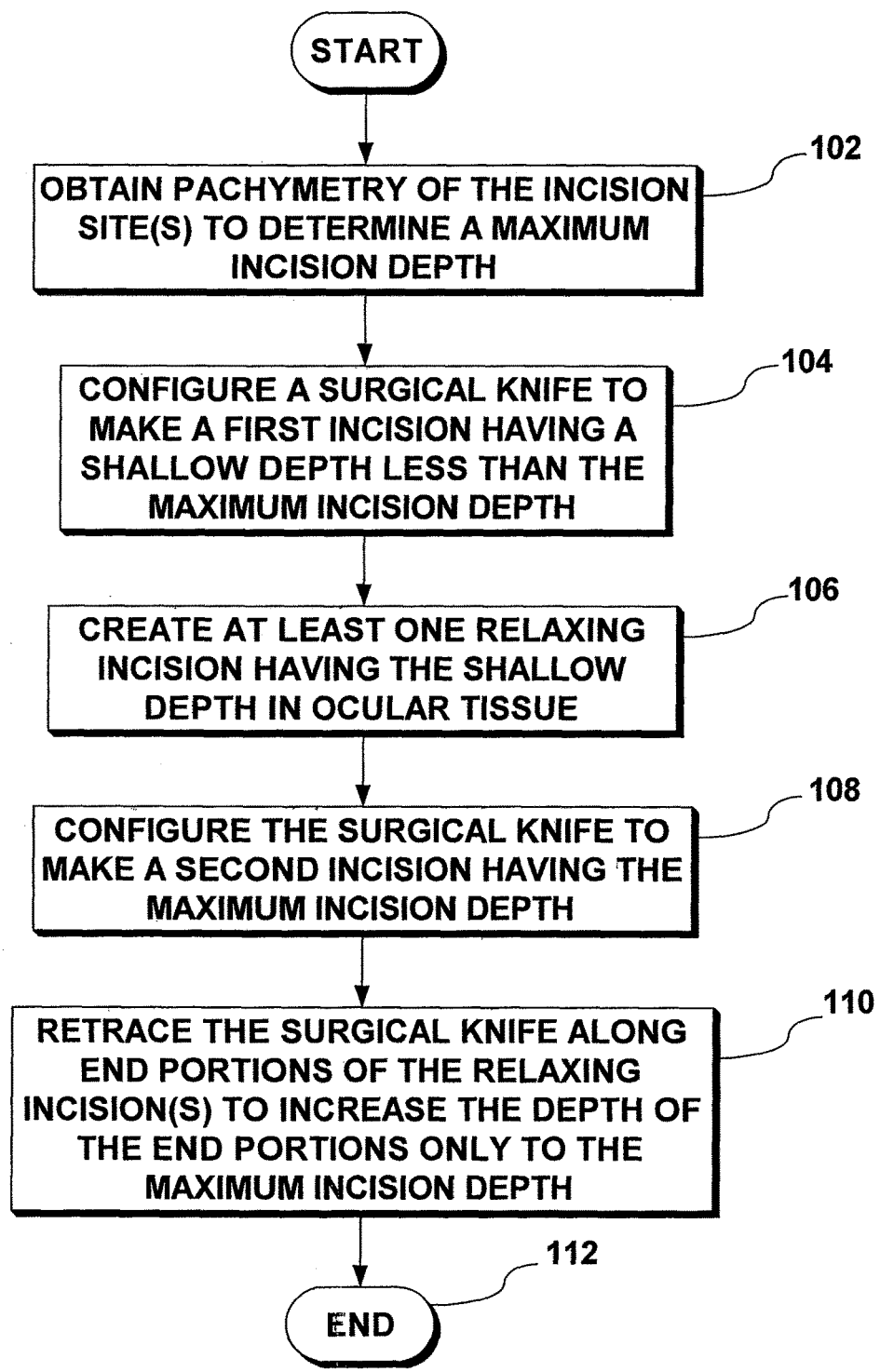
FIG. 6 is a flow diagram illustrating a manual surgical method in accordance with an exemplary embodiment of the present invention.

Referring now to FIG. 6, a flow diagram 100 is shown that illustrates an exemplary manual surgical method in accordance with the present invention. In this exemplary embodiment, the structured incision is configured to have a shallower central portion and deeper end portions that collectively tend to induce a greater relaxing effect toward the end portions of the incision.

As shown in FIG. 6, the exemplary manual method involves use of a conventional surgical knife, such as a Genesis/DuoTrak or other type of diamond-bladed knife. This method first involves obtaining pachymetry of the incision site or sites at which the AK incision(s) is/are to be performed, as shown at step 102. This step may be performed in a conventional manner using an ultrasonic pachymeter, and suitable techniques and equipment for obtaining same are well known in the art. As is typical of this step, such obtaining such pachymetry involves determining a maximum incision depth, e.g., 680 microns.

Next, the method involves configuring a surgical knife to make a first incision pass having a shallow depth less than the maximum incision depth, as shown at step 104. For example, this step may involve adjusting the micrometer of a conventional surgical knife. By way of example, the shallow depth may be approximately 100 to 150 microns less than the maximum depth. In a preferred embodiment, the shallow depth is approximately 150 microns less than the maximum depth. Maximum incision depth is typically equal to or slightly less than the corneal thickness at the incision site.

Next, the method involves creation of at least one relaxing incision (e.g., an LRI or an AK incision) in ocular tissue, as shown at step 106. Generally, this step may be performed in a substantially conventional manner, e.g., as to arcuate shape, placement, length, angle of attack, overall surgical technique, etc. By way of example, this step may include using a Genesis/DuoTrak™-style knife to square off both ends of the incision to bring the entire incision to a constant depth. The incision so created has a depth equal to the shallow depth as a result of the configuration of the knife and conventional surgical procedures.

The surgical knife is then configured to make a deeper incision having the maximum incision depth, as shown at step 108. For example, this step may involve adjusting a micrometer of a surgical knife to provide for a deeper cut.

Finally, the vertical enhancement edge of the surgical knife is retraced along the end portions of the relaxing incision to increase the depth of the incision's end portions only, as shown at steps 110 and 112. The depth of the end portions is increased to the maximum incision depth, consistent with conventional surgical procedures. By way of example, the deepened portions may be configured to extend for approximately 1 mm of length at each end of the incision.

Accordingly, a structured incision is provided that has a greater depth at its end portions, and a lesser depth at its central portion (in a deep-shallow-deep configuration), as best shown in FIG. 7, consistent with the present invention. Using the structured incision technique described, the profile of the incision might be described as resembling the profile (as viewed from the side) of an arch bridge, in that it is deeper at the ends and shallower in the center. By providing a greater depth at the incision's ends where the relaxing effect naturally tends to be less, and a lesser depth toward the central portion where the relaxing effect naturally tends to be greater, a more uniform relaxing effect is provided along the single incision's entire length.

It is noted that intraoperative feedback with a qualitative operative keratometer may be helpful to the surgeon. The reflection of its ring allows assessment of the amount and axis of astigmatism. The flat corneal meridian is identified by the long axis of the ellipse. An additional cue can be obtained if an operative keratometer with a ring of LED's is used, in that the reflections of the individual LED's of the ring are spaced further apart at the steep meridian. Identifying the axis of astigmatism on the operating table serves both to reveal torsion on reclining, and serves as a safeguard against a 90 degree axis error.

Figure 7A:
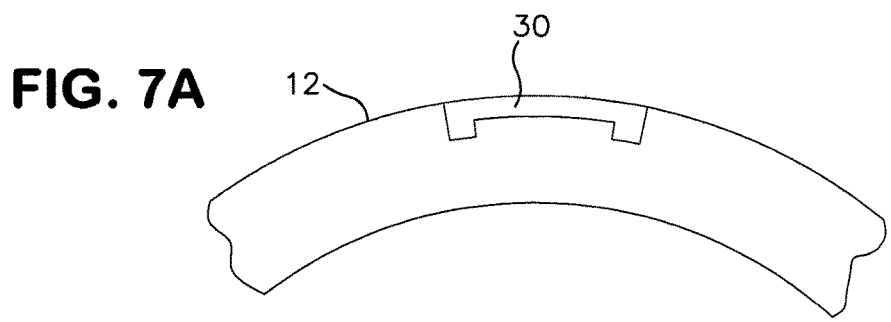
FIG. 7A is a diagrammatic view of the human eye of FIG. 1, showing an embodiment of a structured incision in accordance with the present invention.
Figure 7B:
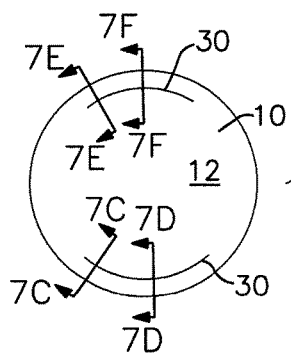
FIG. 7B is a diagrammatic view of the human eye of FIG. 1, showing alternative embodiments of structured incisions in accordance with the present invention.
Figure 7C:
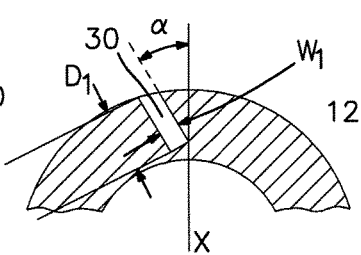
FIGS. 7C and 7D are cross-sectional views of the human eye of FIG. 1 taken along lines 7C-7C and 7D-7D, respectively, of FIG. 7B, showing a variable-depth structured incision.
Figure 7D:
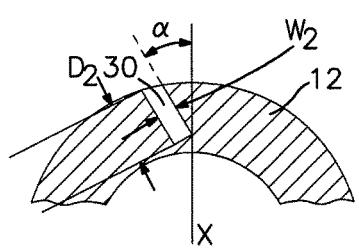

In this exemplary embodiment, it is contemplated that the structured incision has a consistent, or substantially-consistent resulting only from any deviation due to the manual and free-hand nature of the incision, angle of attack ( ) in that the angular orientation of the surgical blade relative to the eye (or a vertical reference plane X) along the length of the incision 30, as best shown in FIGS. 7A, 7B and 7C. As noted from FIGS. 7B and 7C, the depth $D_1$ of the incision 30 at its end portion (FIG. 7B) is greater than the depth $D_2$ of the incision 30 at its central portion (FIG. 7C). However, due to the fixed width of the blade, the width/profile of the incision 30 along its length is substantially uniform (i.e., $W_1=W_2$), absent effects from any resulting relaxation of the eye tissue, as shown in FIGS. 7C and 7D.

Figure 7E:
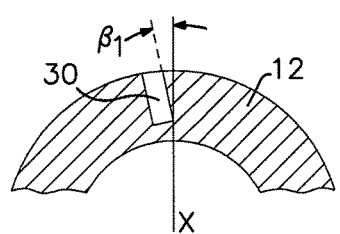
FIGS. 7E and 7F are cross-sectional views of the human eye of FIG. 1 taken along lines 7E-7E and 7F-7F, respectively, of FIG. 7B, showing a variable-angle-of-attack structured incision.
Figure 7F:
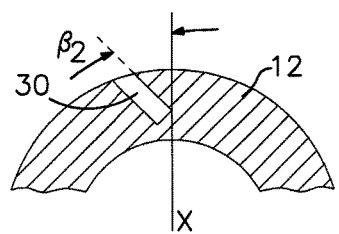

In another embodiment, the structured incision is configured to have a varying angle of attack ($\beta$) that tends to induce a greater relaxing effect toward the end portions of the incision, as best shown in FIGS. 7B, 7E and 7F. In this exemplary embodiment, the width of the incision is constant, and the depth of both incisions is identical. However, in this embodiment the surgical knife is manually manipulated to vary the tilt of the knife along the length of the incision (relative to a surface of the ophthalmic tissue), and thus to vary the angle of attack of the incision 30. In the exemplary embodiment shown, $\beta_2$ is greater than $\beta_1$. In an alternative embodiment, $\beta_1$ is greater than $\beta_2$. In both embodiments, the varying angle of attack ($\beta$) that tends to induce a greater relaxing effect toward the end portions of the incision.

In still other embodiments of the invention, the structured incision includes any combination of more than one of a varying depth, a varying angle of attack and a varying cross-sectional width or shape profile along its length to induce a relatively greater relaxing effect toward the end portions of the incision. It is noted however, that the varying cross-sectional width/profile may not be easily or predictably achieved using a manual method, due to inherent limitations in controlling the knife.

Figure 8:
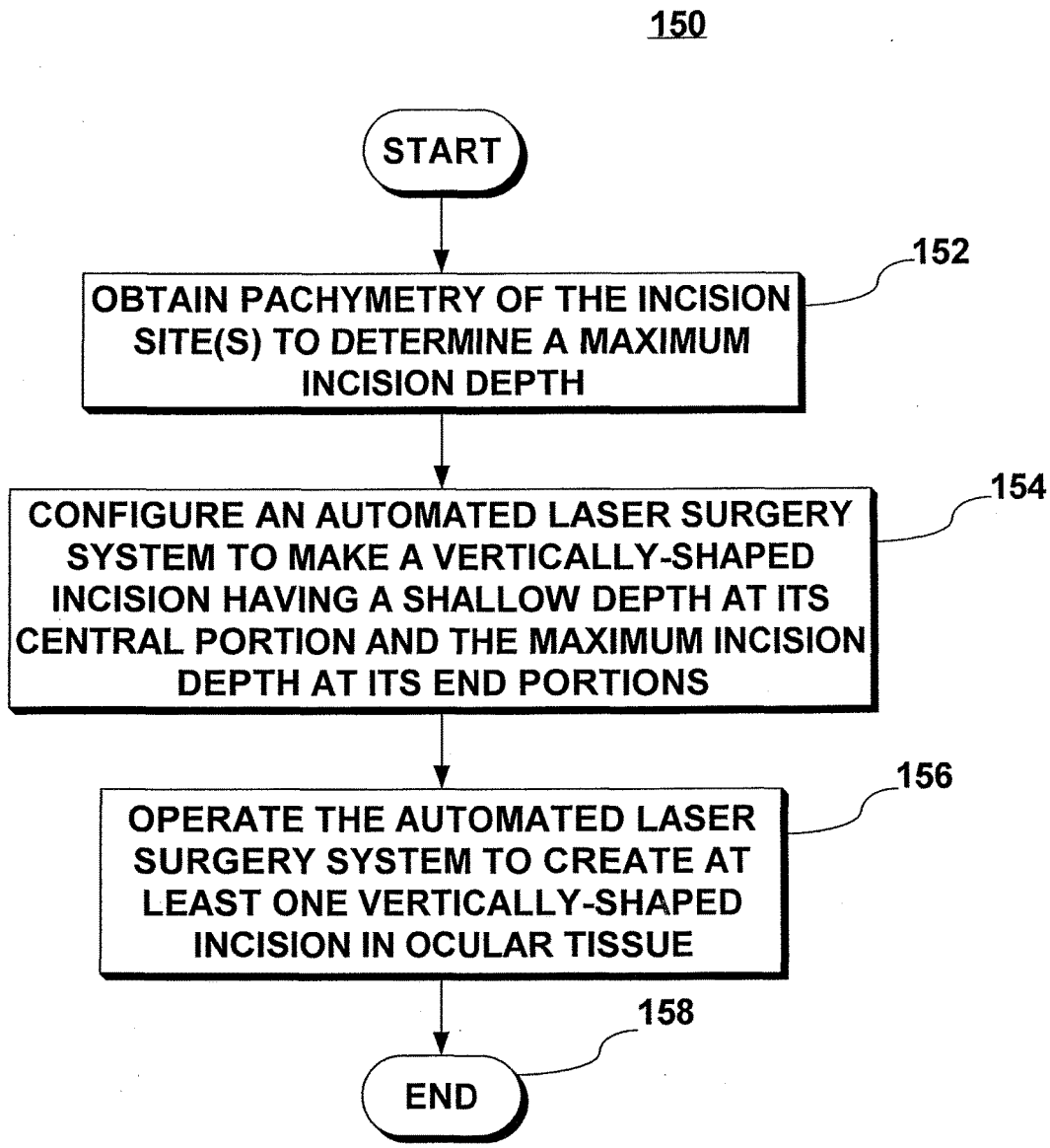
FIG. 8 is a flow diagram illustrating a laser surgery system-based surgical method in accordance with an alternative exemplary embodiment of the present invention.
Figure 10:
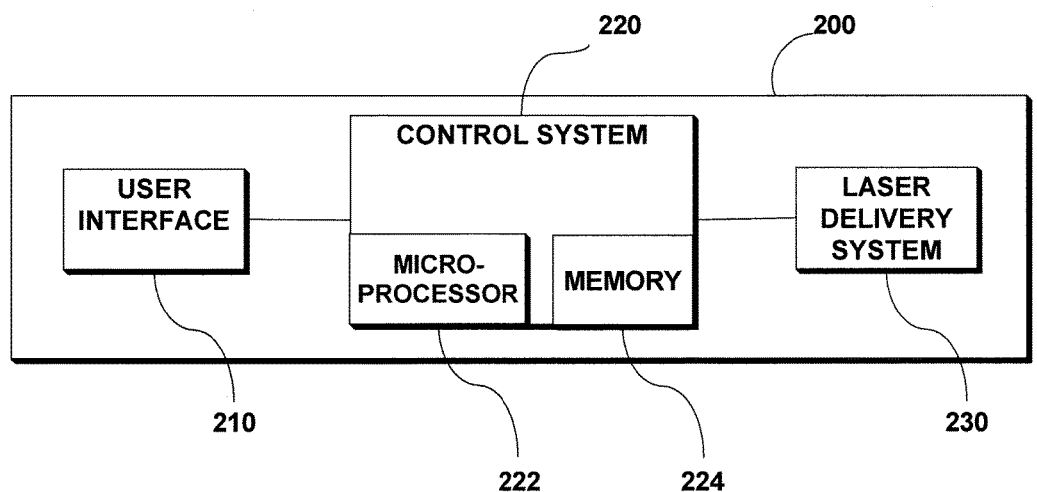
FIG. 10 is a diagrammatic view of an exemplary automated laser surgery system specially-configured to provide a structured incision in accordance with the present invention.

Referring now to FIG. 8, a flow diagram 150 is shown that illustrates an exemplary automated surgical method in accordance with the present invention. As shown in FIG. 8, the exemplary manual method involves use a specially-configured automated laser surgery system 200, as shown in FIG. 10. The specially-configured automated laser surgery system 200 is substantially similar to existing commercially-available automated laser surgery systems. Examples of such automated laser surgery systems include the LensAR, LenSX and Catalys™ femtosecond laser surgery systems presently sold by LensAR, Inc. of Winter Park, Fla., LenSX Lasers, Inc., of Aliso Viejo, Calif. and OptiMedica Corporation of Santa Clara, Calif., respectively. Such existing systems generally include a user interface for receiving user input and imaging, a laser delivery system for creating surgical incisions in ocular tissue of a human patient, and a control system for creating the surgical incisions based upon the user input and consistent with predetermined instructions, logic, parameters, etc.

As noted above, such existing systems, to the extent that they are adapted to create AK incisions based on user (surgeon) input such as optical zone, arc length, incision depth, are configured to do so in accordance with predetermined instructions, logic and/or parameters resident in the control system. Conventional control systems provide for an incision geometry having a constant/uniform depth, a uniform width/profile, and a uniform angle of attack along the length of the AK incision, consistent with conventional wisdom.

The present invention further provides a specially-configured automated laser surgery system 200, as shown in FIG. 10. In accordance with the present invention, the specially-configured automated laser surgery system 200 resembles conventional laser surgery systems, but includes a modified control system 220 that further accepts user input (via a user interface 210) as to maximum, minimum and/or other incision depth parameters, angle of attack parameters, and incision width/profile parameters, and is further configured to create a structured incision (via the laser delivery system 230) in accordance with such user input and predetermined instructions, logic and/or parameters resident in the control system 220 that provides for a structured incision geometry, consistent with the teachings herein.

Programming hardware, software, and techniques necessary to implement the control system 220 described herein are well-known in the art, particularly to existing manufacturers of commercially-available automated laser surgery systems, and are beyond the scope of the present invention, and thus are not discussed in detail herein. Generally, the control system may include a microprocessor 222 and a memory 224 operably connected to the microprocessor. The memory 224 may store microprocessor-executable instructions for controlling the laser delivery system to provide the elongated structured incisions described herein.

The precise configuration of the incision geometry for a particular incision may be based upon explicit user (surgeon) input, may be derived in accordance with predetermined logic from user or other input, or may be otherwise determined, e.g. according to predetermined settings within the control system 220. Any desired structured incision geometry may be used consistent with the present invention, provided that the incision geometry, for example but not limited to depth, angle of attack and cross-sectional width/profile, varies along the length of the incision such that it tends to induce a greater relaxing effect toward the end portions of the incision than at the central portion of the incision. The user interface 210 may provide for any desired additional geometry options.

Figure 9A:
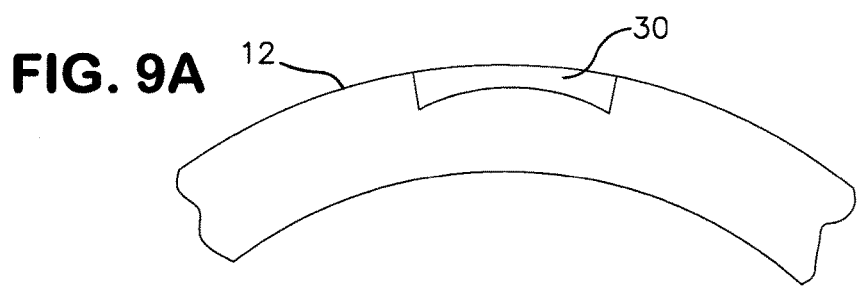
FIG. 9A is a diagrammatic view of the human eye of FIG. 1, showing an alternative embodiment of a structured incision in accordance with the present invention.

The incision geometry created with the laser surgery equipment may have a generally stepped configuration, with discrete portions having distinctly different depths, as shown in FIG. 7A, or distinctly different widths, or angles of attack. However, a potential advantage of use of laser surgery equipment is that the depth, angle of attack, and/or width/profile may be substantially continuously variable along the entire length of the incision. An exemplary structured incision having substantially continuously variable depth along its length is shown in FIG. 9A.

Figure 9B:
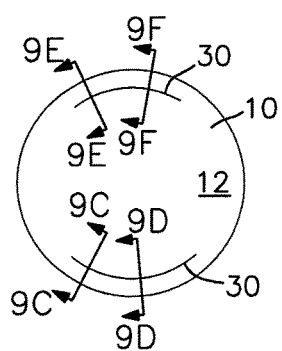
FIG. 9B is a diagrammatic view of the human eye of FIG. 1, showing alternative embodiments of structured incisions in accordance with the present invention.
Figure 9C:
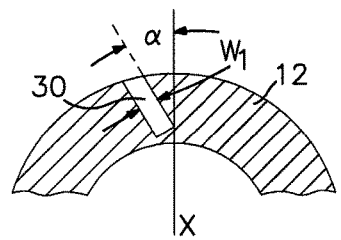
FIGS. 9C and 9D are cross-sectional views of the human eye of FIG. 1 taken along lines 9C-9C and 9D-9D, respectively, of FIG. 9B, showing a variable-width structured incision.
Figure 9D:
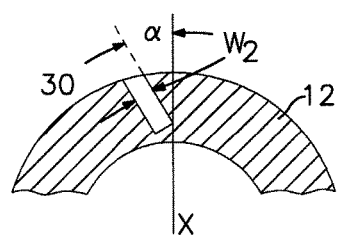

Referring now to FIG. 9B, alternative exemplary structured incisions are shown. An exemplary structured incision 30 having a substantially continuously variable width is shown in FIGS. 9C and 9D, where $W_1$ (toward an end portion of the incision 30) is greater than $W_2$ (toward the central portion of the incision 30). In this example, the angle of attack and depth of the incision are consistent along the incision's length, but it is noted that in other embodiments they may vary.

Figure 9E:
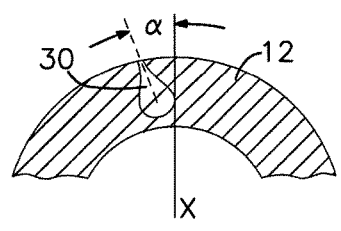
FIGS. 9E and 9F are cross-sectional views of the human eye of FIG. 1 taken along lines 9E-9E and 9F-9F, respectively, of FIG. 9B, showing a variable-profile structured incision.
Figure 9F:
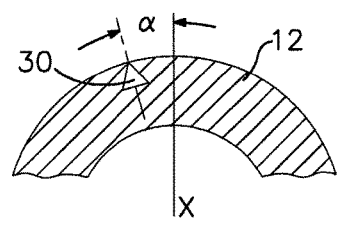

In FIGS. 9C and 9D, it is noted that the cross-sectional profile is consistent (rectangular in this example). In FIGS. 9E and 9F, an exemplary incision 30 having a substantially continuously variable profile is shown. Notable, the cross-sectional area toward an end portion of the incision 30 (FIG. 9E) is greater than the cross-sectional area toward the central portion of the incision 30 (FIG. 9F). In this example, the angle of attack is consistent along the incision's length, but it is noted that in other embodiments it may vary.

The inventive automated laser surgery system 200 may be used in accordance with the flow diagram 150 shown in FIG. 8. Referring now to FIG. 8, the method first involves obtaining pachymetry of the incision site or sites at which the AK incision(s) is/are to be performed, as shown at step 152. As noted above, with respect to a variable-depth structured incision, this involves determining the maximum incision depth, and may be performed in a conventional manner, which may include, for example, obtaining such pachymetry using the automated laser surgery system 200. By way of example, this may involve various imaging technologies, such as optical coherence tomography, Scheimpflug photography, or confocal microscopy.

Next, the method involves configuring the automated laser surgery system 200 to make a structured incision. In this example, the structured incision is a variable-depth structured incision having a shallow depth at its central portion and the maximum incision depth at its end portions, as shown at step 154. By way of example, this may involve entering incision optical zone, meridian, length, maximum depth, minimum depth, angle of attack parameters, width parameters, profile parameters and any other variable geometry input via the user interface 210 of the automated laser surgery system 200.

Finally, the method involves operating the automated laser surgery system 200 to create at least one structured incision in ocular tissue, and the method ends, as shown at steps 156 and 158. For the surgeon, this step may be as simple as selecting a "START PROCEDURE" option via the user interface, but generally this step involves causing the control system 220 of the automated laser surgery system 200 to control the laser delivery system 230 to delivery laser energy to the necessary locations (focal spots) in the patient's ocular tissue to define the desired structured incision consistent with the surgeon's input and any other applicable predetermined instructions, logic and/or parameters resident in the control system 220.

It should be noted that the computer-controlled and/or mechanized aspects of laser surgery equipment are well-suited to provide continuously-variable incision geometry generally unobtainable using manual techniques. Further, such targeted ablation equipment is capable of providing structured incision geometries that cannot be created manually with a surgical blade. For example, the structured incision geometries in accordance with the present invention may be entirely intrastromal. Incisions that do not connect with the surface could be manually spread, or left unspread. Further, such equipment is well-suited to permitting intra-operative modifications to the incision, e.g., to deepen, lengthen or modify curvature of the incision).

Advantageously, the present invention is compatible with paired LRI's. Paired LRIs have several advantages over a single, longer LRI. First, they allow shorter incisions. The longer an incision is, the less regular its effect. Second, a single incision flattens only a single hemi-meridian; paired incisions have a more symmetric effect. In treating against-the-rule astigmatism, the temporal cataract incision may serve as the second LRI of the pair, particularly if a Langerman groove is made.

Advantages of the structured incision technique over the traditional LRI technique include improved predictability of the astigmatic effect and reduction of induced higher order aberrations. Much of the variability in astigmatic effect of traditional LRI's may be ascribed to variability in the proportion of the incision that is actually at the intended depth. Because with the structured incision technique, the entire incision is fully effective, incisions may be shorter and/or more peripheral for a given astigmatic correction. Shorter incisions and more peripheral incisions induce less aberration, and even less aberration is induced if the incisions are deeper at the ends than at the center.

Advantages of the structured incision technique over "C" techniques such as those described by Canrobert Oliveira and by Freitas and Carvalho include the structured incision technique's being easier, faster and safer. It is more readily standardized, yet no template is required. Furthermore, a pair of single incisions is more readily enhanced than a pair of triple arcs.

In summary, the central portion of a traditional AK incision naturally has greater effect than the end portions, and this effect may induce aberration as well as astigmatism at a new axis. This problem can be prevented by constructing a structured incision designed to induce (absent the natural non-uniform effect) a greater relaxing/corrective effect its end portions than at its central portion, such that non-uniform relaxing due to the structure of the incision combines with the non-uniform natural relaxing of the incision to cause a more consistent relaxing effect along the entire length of the incision.

By way of further example, the method and system of the present invention may be used as follows with respect to an exemplary 73-year-old man having 1.25 diopters of with-the-rule astigmatism in the right eye, and for which preoperative keratometry measures 44.50/43.25D with the steep meridian at 90 degrees. Superior and inferior limbal relaxing incisions at the 9 mm optical zone may be planned. The Lindstrom ARC-T 8-9 mm nomogram predicts that for a 73-year-old, two 30 degree incisions at the 8 to 9 mm optical zone would give 0.93 diopters of correction, and two 45° incisions would give 1.86 diopters of correction. Because incisions whose ends are brought to full depth give more effect than typical LRI incisions, the nomogram may be been modified. Since the temporal clear corneal cataract incision was predicted to contribute 0.50 diopters of with-the-rule astigmatism, a total of 1.75 diopters correction may be required. A decision may be made to make a 35° superior limbal relaxing incision and a 30° inferior limbal relaxing incision at the 9 mm optical zone.

In this example, it may be considered that the thinnest central pachymetry is 520 microns; the superior incision site's pachymetry is 662 microns and the inferior incision site's is 656. For a manual incision, a Genesis/DuoTrak knife may be set at 555 microns [655 minus 100 microns] initially. For an automated laser surgery system, such a depth of cut may be input via the user interface of the system 200.

After preparing and draping the patient, but before the cataract procedure has begun, torsion on reclining may be assessed using the operative keratometer or other imaging technology. To avoid induction of artifactual astigmatism, the lid speculum may be held away from the globe while the astigmatic axis is assessed using the keratometer's ring reflection or other technology. In this example, 20 degrees of torsion is revealed by the rotation of the elliptical operative keratometer reflection or other technology. The astigmatic incisions may then be created at the proper meridian at a depth of 505 microns, and then each end of each incision is "squared off" to the full 505 micron depth using the vertical "enhancement" edge of the blade. This edge is then used to deepen the ends of each incision to full incision depth, in this case 655 microns. Alternatively, the laser system 200 may be used to perform such an incision, or any other desired structured incision.

Postoperatively, keratometry may be measured as 43.87/43.75 D with the steep meridian at 90 degrees and manifest refraction is −0.75 sphere. Elevation corneal topography suggested similar astigmatic effect in the center and at the ends of the incision.

While there have been described herein the principles of the invention, it is to be understood by those skilled in the art that this description is made only by way of example and not as a limitation to the scope of the invention, and that various changes in detail may be effected therein without departing from the spirit and scope of the invention as defined by the claims.

What is claimed is:

1. A method for performing ophthalmic laser surgery, the method comprising:
   determining an expected variation in post-surgical relaxation of ocular tissue along an incision site;
   providing an automated laser surgery system comprising:
      a laser delivery system operable to deliver a laser beam for ablating ocular tissue;
      a user interface configured to receive user input; and
      a laser control system configured to control delivery of the laser beam in accordance with input received via the user interface; and
   operating the automated laser surgery system to selectively ablate ocular tissue to provide an elongated structured incision extending in arcuate fashion across the steep meridian of the cornea, the structured incision being structured to be non-uniform along its length, the non-uniformity being specifically configured to counteract the expected variation in post-surgical relaxation of ocular tissue, and thus to provide an improved corrective effect, wherein operating the automated laser surgery system to selectively ablate ocular tissue to provide an elongated structured incision comprises ablation of tissue to provide an incision having a greater depth of cut at its end portions than at its central portion.

2. A method for performing ophthalmic laser surgery, the method comprising:
   determining an expected variation in post-surgical relaxation of ocular tissue along an incision site;
   providing an automated laser surgery system comprising:
      a laser delivery system operable to deliver a laser beam for ablating ocular tissue;
      a user interface configured to receive user input; and
      a laser control system configured to control delivery of the laser beam in accordance with input received via the user interface; and
   operating the automated laser surgery system to selectively ablate ocular tissue to provide an elongated structured incision extending in arcuate fashion across the steep meridian of the cornea, the structured incision being structured to be non-uniform along its length, the non-uniformity being specifically configured to counteract the expected variation in post-surgical relaxation of ocular tissue, and thus to provide an improved corrective effect, wherein operating the automated laser surgery system comprises operating the automated laser surgery system to selectively ablate ocular tissue to provide an elongated structured incision that is nonuniform in at least one of angle of attack relative to a surface of the ocular tissue, profile, and width.

3. The method of claim 2, wherein operating the automated laser surgery system to selectively ablate ocular tissue to provide an elongated structured incision comprises ablation of tissue to provide an incision having a greater width of cut at its end portions than at its central portion, the width being measured transversely to a direction of elongation of the structured incision.

4. The method of claim 2, wherein operating the automated laser surgery system to selectively ablate ocular tissue to provide an elongated structured incision comprises ablation of tissue to provide an incision having a larger cross-sectional profile at its end portions than at its central portion, the cross-sectional profile extending transversely to a direction of elongation of the structured incision.

5. The method of claim 2, wherein operating the automated laser surgery system to selectively ablate ocular tissue to provide an elongated structured incision comprises ablation of tissue to provide an incision having a greater angle of attack at its central portion than at its end portions, the angle of attack being measured transversely to a direction of elongation of the structured incision.

6. An automated laser surgery system comprising:
   a laser delivery system operable to deliver a laser beam for ablating ophthalmic ocular tissue;
   a user interface configured to receive user input; and
   a laser control system operably connected to said laser delivery system and said user interface, said laser control system being configured to control delivery of the laser beam in accordance with input received via said user interface, said laser control system being configured to control said laser delivery system to cause the laser beam to selectively ablate ocular tissue to provide an elongated structured incision that extends along a surface of the ocular tissue and varies, along its length, in perimeter of cross-section taken transversely to a direction of elongation of the structured incision, the non-uniformity of the cross-section being designed to complement expected post-surgical relaxing of ocular tissue to provide an improved corrective effect, wherein the laser control system is configured to control said laser delivery system to cause the laser beam to selectively ablate ocular tissue to provide an elongated structured incision that varies along its length in at least one of angle of attack relative to a surface of the ocular tissue, profile, and width.

7. An automated laser surgery system comprising:
   a laser delivery system operable to deliver a laser beam for ablating ophthalmic ocular tissue;
   a user interface configured to receive user input; and
   a laser control system operably connected to said laser delivery system and said user interface, said laser control system being configured to control delivery of the laser beam in accordance with input received via said user interface, said laser control system being configured to control said laser delivery system to cause the laser beam to selectively ablate ocular tissue to provide an elongated structured incision that extends along a surface of the ocular tissue and varies, along its length, in perimeter of cross-section taken transversely to a direction of elongation of the structured incision, the non-uniformity of the cross-section being designed to complement expected post-surgical relaxing of ocular tissue to provide an improved corrective effect, wherein the laser control system is further configured to control the laser beam to provide an incision having a greater depth of cut at its end portions than at its central portion.

8. The system of claim 7, wherein the laser control system is further configured to control the laser beam to provide an incision having a depth of cut that is substantially continuously variable along its length.

9. An automated laser surgery system comprising:
a laser delivery system operable to deliver a laser beam for ablating ophthalmic ocular tissue;
a user interface configured to receive user input; and
a laser control system operably connected to said laser delivery system and said user interface, said laser control system being configured to control delivery of the laser beam in accordance with input received via said user interface, said laser control system being configured to control said laser delivery system to cause the laser beam to selectively ablate ocular tissue to provide an elongated structured incision that extends along a surface of the ocular tissue and varies, along its length, in perimeter of cross-section taken transversely to a direction of elongation of the structured incision, the non-uniformity of the cross-section being designed to complement expected post-surgical relaxing of ocular tissue to provide an improved corrective effect, wherein the laser control system is further configured to control the laser beam to provide an incision having a greater width of cut at its end portions than at its central portion, the width being measured transversely to a direction of elongation of the structured incision.

10. The system of claim 9, wherein the laser control system is further configured to control the laser beam to provide an incision having a width of cut is substantially continuously variable along its length.

11. An automated laser surgery system comprising:
a laser delivery system operable to deliver a laser beam for ablating ophthalmic ocular tissue;
a user interface configured to receive user input; and
a laser control system operably connected to said laser delivery system and said user interface, said laser control system being configured to control delivery of the laser beam in accordance with input received via said user interface, said laser control system being configured to control said laser delivery system to cause the laser beam to selectively ablate ocular tissue to provide an elongated structured incision that extends along a surface of the ocular tissue and varies, along its length, in perimeter of cross-section taken transversely to a direction of elongation of the structured incision, the non-uniformity of the cross-section being designed to complement expected post-surgical relaxing of ocular tissue to provide an improved corrective effect, wherein the laser control system is further configured to control the laser beam to provide an incision having a greater cross-sectional profile at its end portions than at its central portion, the cross-sectional profile extending transversely to a direction of elongation of the structured incision.

12. The system of claim 11, wherein the laser control system is further configured to control the laser beam to provide an incision having a cross-sectional profile that is substantially continuously variable along its length.

13. An automated laser surgery system comprising:
a laser delivery system operable to deliver a laser beam for ablating ophthalmic ocular tissue;
a user interface configured to receive user input; and
a laser control system operably connected to said laser delivery system and said user interface, said laser control system being configured to control delivery of the laser beam in accordance with input received via said user interface, said laser control system being configured to control said laser delivery system to cause the laser beam to selectively ablate ocular tissue to provide an elongated structured incision that extends along a surface of the ocular tissue and varies, along its length, in perimeter of cross-section taken transversely to a direction of elongation of the structured incision, the non-uniformity of the cross-section being designed to complement expected post-surgical relaxing of ocular tissue to provide an improved corrective effect, wherein the laser control system is further configured to control the laser beam to provide an incision having a greater angle of attack at its central portion than at its end portions, the angle of attack being measured transversely to a direction of elongation of the structured incision.

14. The system of claim 13, wherein the laser control system is further configured to control the laser beam to provide an incision having an angle of attack that is substantially continuously variable along its length.

* * * * *